United States Patent
Valenta et al.

(10) Patent No.: US 7,485,305 B2
(45) Date of Patent: Feb. 3, 2009

(54) ALLERGEN FROM HOUSE-DUST MITES

(75) Inventors: Rudolf Valenta, Theresienfeld (AT); Peter Valent, Vienna (AT); Margit Weghofer, Vienna (AT); Susanne Vrtala, Vienna (AT); Maria-Theresia Krauth, Tribuswinkel (AT)

(73) Assignee: Biomay AG, Vienna (AT)

( * ) Notice: Subject to any disclaimer, the term of this patent is extended or adjusted under 35 U.S.C. 154(b) by 0 days.

(21) Appl. No.: 11/141,642

(22) Filed: Jun. 1, 2005

(65) Prior Publication Data

US 2006/0002948 A1   Jan. 5, 2006

(30) Foreign Application Priority Data

Jul. 1, 2004   (EP) .................................. 04015448

(51) Int. Cl.
- *A61K 39/00* (2006.01)
- *A61K 39/35* (2006.01)
- *C07K 1/00* (2006.01)
- *C07K 14/00* (2006.01)
- *C07K 16/00* (2006.01)

(52) U.S. Cl. ................. 424/185.1; 424/275.1; 530/350; 530/387.1; 530/387.9; 530/806

(58) Field of Classification Search ........................ None
See application file for complete search history.

(56) References Cited

U.S. PATENT DOCUMENTS 6,689,876 B1   2/2004   Thomas et al.

FOREIGN PATENT DOCUMENTS

WO   WO 2004/007542 A1   1/2004

OTHER PUBLICATIONS

Sergel, T.A., et al. 2000 J Virology 74(11): 5101-5107.*
Burks, A.W., et al. 1997 European Journal of Biochemistry 245: 334-339.*
Kumar, V., et al. 1990 Proc. Natl. Acad. Sci. 87: 1337-1341.*
Yuan, S-M., et al. 1998 Proteins 30: 136-143.*
(SMIK) Smithkline Beecham Corp.: "Amino acid sequence of an alkyl hydroperoxide reductase F52A protein", Aug. 27, 1997, Database EMBL 'Online!, Database accession No. AAW28175, amino acid residues 32-38.
(CORI-) Corixa Corp.: "Propionibacterium acnes immunogenic protein #10750", Feb. 13, 2002, Database EMBL 'Online!, Database accession No. AAU49854 amino acid residues 21-27.
Rudolf Valenta, "The future of antigen-specific immunotherapy of allergy", Nature, Jun. 2002, pp. 446-453, vol. 2.
G. Pittner et al., "Component-resolved diagnosis of house-dust mite allergy with purified natural and recombinant mite allergens", Clin Exp Allergy, 2004, pp. 597-603, vol. 34.
Ball, Tanja et al., "B Cell Epitopes of the Major Timothy Grass Pollen Allergen, Phl p 1, revealed by gene fragmentation as candidates for Immunotherapy", The FASEB Journal, vol. 13, Aug. 1999, pp. 1277-1290, USA.
Ebner, Christof et al., "T Cell Clones Specific for Bet v 1, the major birch pollen allergen, cross-react with the major allergens of Hazel, Cor a I, and Alder, Aln g I", Molecular Immunology, vol. 30, No. 15, pp. 1323-1329, 1993, printed in Great Britain.
Ebner, Christof, et al., "Allergens, IgE, mediators, inflammatory mechanisms: Identification of allergens in fruits and vegetables: IgE cross-reactivities with the important birch pollen allergens Bet v 1 and Bet v 2 (birch profiling)", J Allergy Clin Immunol, vol. 95, No. 5, Part 1, pp. 962-969, USA.
Focke, M. et al., "Non-anaphylactic surface-exposed peptides of the major birth pollen allergen, Bet v 1, for preventive vaccination", Clinical and Experimental Allergy, 34:1525-1533, 2004 Blackwell Publishing Ltd.
Focke, Margarete et al., "Nonanaphylactic synthetic peptides derived from B cell epitopes of the major grass pollen allergen, Phl p 1, for allergy vaccination", The FASEB Journal, vol. 15, Sep. 2001, pp. 2042-2044, USA.
Fritsch, Ruth et al., "Bet v 1, the major birch pollen allergen, and Mal d 1, the major apple allergen, cross-react at the level of allergen-specific T helper cells", J Allergy Clin Immunol, Oct. 1998, pp. 679-686, USA.
Punnonen, Juha, "Molecular Breeding of Allergy Vaccines and Antiallergic Cytokines", Int Arch Allergy Immunol 2000; 121:173-182, Basel, CH.

* cited by examiner

*Primary Examiner*—Jon Weber
*Assistant Examiner*—Marsha M Tsay
(74) *Attorney, Agent, or Firm*—Arent Fox LLP

(57) ABSTRACT

The present invention relates to a novel allergen from house-dust mites, to polypeptides derived from said allergen and polynucleotides encoding the same. Furthermore, the invention provides antibodies directed against the allergen and to the use of the polypeptides, polynucleotides and/or antibodies in therapy and diagnosis of allergic disorders.

12 Claims, 7 Drawing Sheets

Figure 1A

Figure 1B:
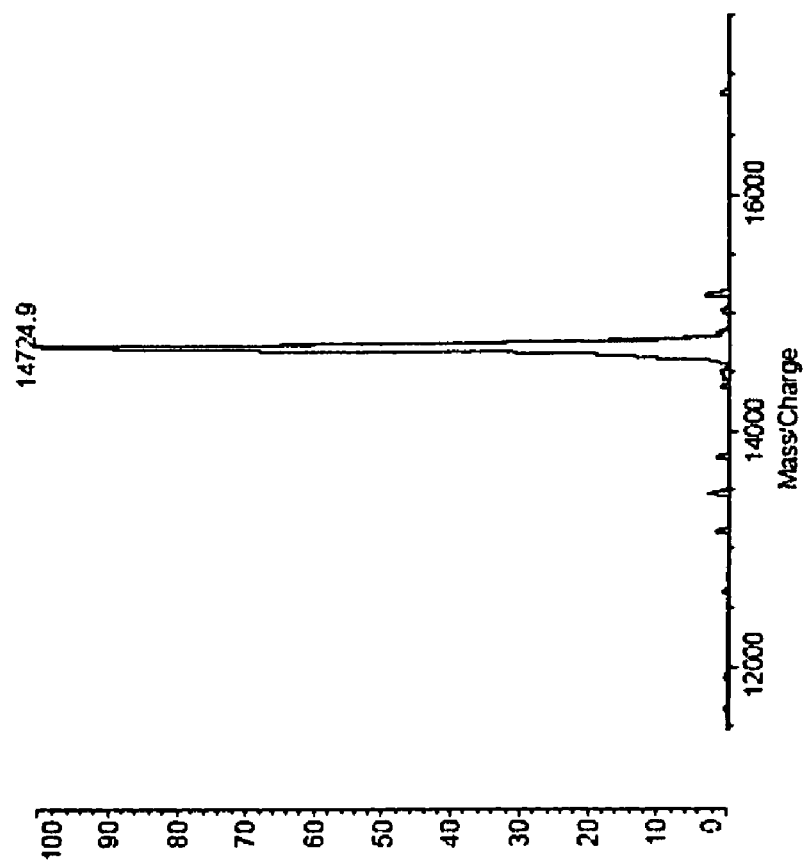
Figure 1B:
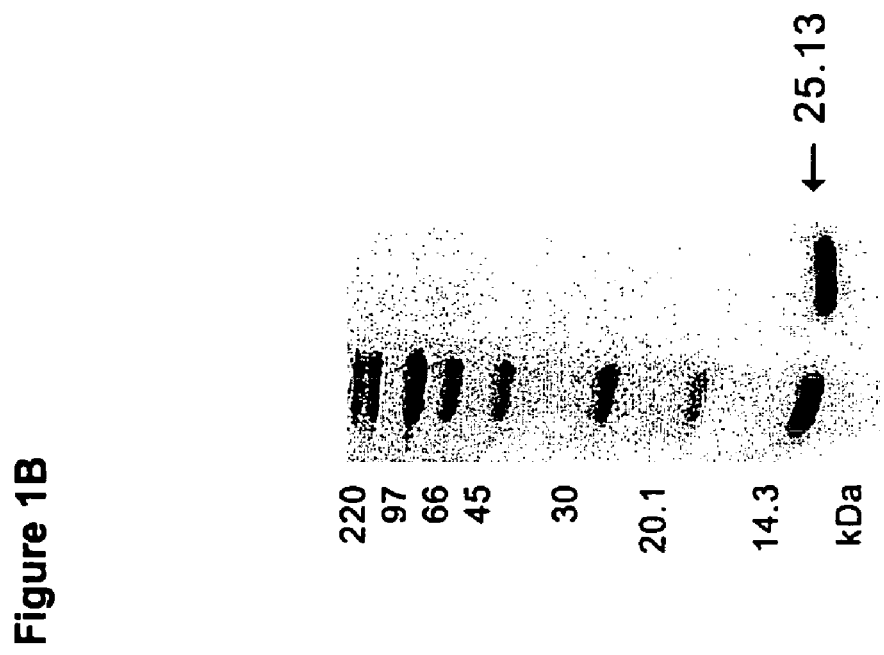

```
1   aaaaaaagaaattttttcaaaa ATG AAA TTC ATC ATT ACC CTT              7
                           M   K   F   I   I   T   L 45  TTC GCT GCC ATT GTA ATG GCT GCC ATT GTA TCT GGT TTT            20
    F   A   A   I   V   M   A   A   I   V   S   G   F 84  ATT GTT GGT GAC AAA ATG GAT GAA TGG CGT ATG GCA                33
    I   V   G   D   K   M   D   E   W   R   M   A 123 TTC GAT CGT TTA ATG GAA AAA ATG GAA ACA AAA ATC                46
    F   D   R   L   M   E   E   M   E   T   K   I 162 GAT CAA GTT GAA GGT GAA AAA GGT TTA CTT CAT AGT GAA CAA        59
    D   Q   V   E   G   E   K   G   L   L   H   S   E   Q 201 TAC AAA GAA TTG GAA AAA ACC AAA AGC ACT ATT GGT GAA TTT AAA    72
    Y   K   E   L   E   K   T   K   S   K   I   G   E   L   K 240 GAA CAA ATT CTT CGT GAA TTT ACT TTC GAA ATG GAA GCT AAA        85
    E   Q   I   L   R   E   F   T   F   E   M   E   A   K 279 ATG AAA GGT GCA TTA AAT ATG TTT AAA TTA TTG ATT AAA AAA TTG    98
    M   K   G   A   L   N   M   F   K   L   L   I   K   K   L 318 CGT ACC GAT TTA AAT ATG AGT ATT AAA AAA GTT AAA GCT GTA AAT    111
    R   T   D   L   N   M   S   I   K   K   V   K   A   V   N 357 TTT GCT TTG GAA AAA TTA TTG ATT AAA AAA AAA TTG    124
    F   A   L   E   K   L   L   I   K   K   K   L 396 GAC GAA TTG GCT AAA AAA GTT AAA GCT GTA AAT CCG GAT            137
    D   E   L   A   K   K   V   K   A   V   N   P   D 435 GAA TAT TAT taatttaatcgacattaatccaaaaatgtttccaaaat
    E   Y   Y 483 aaaaattttctcttataaaaaaaaaaaa
```

| Recombinant protein | Patient's IgE reactivity (n=117) | Percentage of IgE reactivity |
|---|---|---|
| Clone 25-derived allergen | 30 | 26 |

Figure 2A

Figure 3A

```
         1                                          21                                         41
         MKFIITLFAA  IVMAAAVSGF  IVGDKKEDEW  RMAFDRLMME  ELETKIDQVE
Lep d 5  ---A-V-I-C  FAASVLAQEH  ...KP-K-DF       -DF  -NE----LIH  MT-EQFAKL-
Blo t 5  -----AF-V-  TLAVMT----  ..-E---H--Y  QNE--F-L--  -NE--H-LI-  QANHA-EKG-
Der p 5                                                              RIHEQ-KKG- 61                                         81
         KGLLHLSEQY  KELEKTKSKE  LKEQILRELT  IGENFMKGAL  KFFEMEAKRT
Lep d 5  QA-A---H-V  T----S---  -A----IS  --LD-IDS-K  GH---R-L--A
Blo t 5  HQ--Y-QH-L  D--NEN----  -Q-K-I---D  VVCAMIE--Q  GAL-R-L---
Der p 5  LA-FY-Q---I  NHF-EKPT--  M-DK-VA-MD  TIIAMID-VR  GVLDRLMQ-K 101                                        121
         DLNMFERYNY  EFALESIKLL  IKKLDELAKK  VKAVNPDEYY
Lep d 5  ---LA-KF-F  -S--STGAV-  H-D-TA--T-  ---IETK
Blo t 5  ---IL--F--  -E-QTLS-I-  L-D-K-TEQ-  --DIQTQ
Der p 5  ---DI--Q--L  -M-KK-GDI-  ERD-KKEEAR  --KIEV
```

ALLERGEN FROM HOUSE-DUST MITES

This application claims priority to European Patent Application No. 04.015448.6 filed Jul. 1, 2004, which is hereby incorporated by reference in its entirety.

The present invention relates to novel allergens from house-dust mites, to polypeptides derived from said allergens and polynucleotides encoding the same. Furthermore, the invention provides antibodies directed against the allergen and to the use of the polypeptides, polynucleotides and/or antibodies in therapy and diagnosis of allergic disorders.

More than 25% of the population suffers from IgE-mediated allergies. Allergic patients are characterized by the increased production of IgE antibodies against per se harmless antigens (i.e., allergens). The immediate symptoms of Type I allergy (allergic rhinoconjunctivitis, asthma, dermatitis, anaphylactic shock) are caused by allergen-induced cross-linking of mast cell-bound IgE antibodies and the release of biologically active mediators (e.g., histamine, leukotriens).

House-dust mites (HDMs) represent one of the most important allergen sources worldwide. Almost 10% of the population and more than 50% of allergic patients are sensitized to mite allergens. The HDM *Dermatophagoides pteronyssinus* (Der p) represents the major indoor allergen source in Central Europe (1). The allergens of Der p comprise more than 30 proteins or glycoproteins, which show cross-reactivity to allergens from other mite species. Nineteen groups of allergens have been characterized so far. Among the 19 described groups of HDM allergens, group 1 and 2 (Der p 1 and Der p 2) represent the most important allergens, but also other HDM allergens (e.g., Der p 5 and Der p 7) were shown to represent important Der p allergens which are recognized by about 50% of Der p allergic patients (2).

Crude HDM extracts, which are currently used for diagnosis and therapy of HDM allergic patients, are only standardized for Der p 1 and Der p 2, whereas other important allergens are only present in small amounts in HDM extracts. Therefore, HDM-specific immunotherapy seems to be less efficient than immunotherapy with pollen allergens. The use of recombinant allergens for diagnosis and therapy could circumvent this problem.

Therefore, a technical problem underlying the present invention is to identify and to isolate novel allergens responsible for allergy or sensitisation to HDM.

The solution to the above technical problem is provided by the embodiments of the present invention characterised in the claims.

In particular, the inventors succeeded in the identification of a new Der p allergen which is useful for diagnosis and therapy of Der p allergic patients. The cDNA coding for this new mite allergen was isolated from a Der p expression cDNA library and expressed in *Escherichia coli* (*E. coli*) as recombinant allergen. The new allergen with a molecular weight of 14.7 kDa binds IgE from around 30% of mite allergic patients. An approximately 50% identity could be found between the aminoacid sequences of the new Der p allergen and of group 5 allergens from different HDM and storage mites (i.e., Der p, *Lepidoglyphus destructor, Blomia tropicalis*). However, no cross-reactivity between the newly described allergen and Der p 5 could be detected, demonstrating that this new allergen represents a new group of HDM allergens. Additionally, the inventors show that recombinant allergen is biologically active. In particular, the allergen released maximal histamine from mite allergic patients' basophils already at a concentration of 10 pg/ml and, in certain cases, could be shown to be even more active than the major allergen, Der p 1, which released maximal histamine only at a concentration of 1 ng/ml.

Therefore, the present invention provides to a polypeptide showing cross-reactivity to polypeptides comprising the amino acid sequence shown in SEQ ID NO 1, in particular amino acids 20 to 140 thereof. The term "cross-reactivity" means that a particular immunoglobulin, preferably an IgE antibody, or a fragment or derivative thereof displaying binding properties of the complete immunoglobulin to epitopes, which binds to the amino acid sequence shown in SEQ ID NO 1 also binds to the polypeptide in question, since said polypeptide in question has an amino acid sequence which comprises at least one epitope or determinant that is recognised by said particular immunoglobulin (preferably IgE) in the polypeptide having the amino acid sequence shown in SEQ ID NO 1. This means that the cross-reactive polypeptide may be capable of triggering allergic reaction or at least sensitisation in an individual being exposed to the cross-reactive polypeptide.

The present invention further relates to a polypeptide comprising an amino acid sequence which has an identity of at least 70% to the amino acid sequence shown in SEQ ID NO 1. Preferably, the polypeptide comprises an amino acid sequence having an identity of at least 75%, more preferably an identity of at least 80%, even more preferably an identity of at least 90%, most preferably an identity of at least 95% to the amino acid sequence shown in SEQ ID NO 1. As used herein, the term "polypeptide" refers to proteins and/or peptides having a length of at least 7 amino acids.

The degree of identity of an amino acid sequence to SEQ ID NO 1 is determined by comparing the amino acid sequence in question and SEQ ID NO 1 using the program "BLAST 2 SEQUENCES (blastp)" (Tatusova et al. (1999) FEMS Microbiol. Lett. 174, 247-250) with the following parameters: Matrix BLOSUM62; Open gap 11 and extension gap 1 penalties; gap x_dropoff50; expect 10.0 word size 3; Filter: none. According to the present invention, the sequence comparison covers at least 40 amino acids, preferably at least 80 amino acids, more preferably at least 100 amino acids, and most preferably at least 120 amino acids.

According to a preferred embodiment the polypeptide of the present invention comprises the amino acid sequence shown in SEQ ID NO 1, more preferably the residues 20 to 140 of the sequence shown in SEQ ID NO 1.

Furthermore, the present invention provides polypeptides comprising a fragment of at least 18 (consecutive) amino acids of the amino acid sequence shown in SEQ ID NO 1. Preferably, the length of the fragment is at least 21 amino acids, more preferably at least 25 amino acids, even more preferably at least 35 amino acids, most preferably at least 50 amino acids of the amino acid sequence shown in SEQ ID NO 1.

A further embodiment of the present invention is a polypeptide consisting of at least 7 (consecutive) amino acids of the amino acid sequence shown in SEQ ID NO 1. Preferably, the length of said polypeptide is at least 10 amino acids, more preferably at least 15 amino acids, even more preferably at least 25 amino acids, most preferably at least 35 amino acids. In further embodiments, the polypeptide of the present invention consists of at least 8 or at least 9 or at least 11 or at least 12 or at least 13 or at least 14 or at least 18 or at least 21 or at least 30 contiguous amino acids of the amino acid sequence shown in SEQ ID NO 1. In further embodiments, the length of the polypeptide is not greater than 100 or 50 or 30 amino acids. Polypeptides consisting of at least 7 amino acids can be recognised by T cells (T cell epitopes).

A further embodiment of the present invention is a polypeptide comprising a fragment of the amino acid sequence shown in SEQ ID NO 1 wherein said fragment is capable of binding to IgE antibodies from an individual being allergic or sensitised against house-dust mites. The term "IgE" antibodies means an antibody preparation which is obtainable by per se known methods. In susceptible humans, exposure to allergens leads to an immediate type (IgE-mediated) allergic response which comprises two steps:

(i) On the first exposure, allergenic proteins induce IgE synthesis by B cells (Vercelli and Geha (1989), J. Allergy Clin. Immunol. 9, 75-83). These specific IgE antibodies then bind to the surfaces of mast cells and basophils via high-affinity Fcε receptors (FcεRI).

(ii) On subsequent exposure, allergens bind and crosslink these specific IgE antibodies leading to the release of pre-formed and newly synthesised inflammatory mediators (e.g. histamine) and chemotactic substances (e.g. platelet-activating factor).

In step (i) above, the production of allergen-specific IgE by B lymphocytes requires the "help" of T lymphocytes (cf. Vercelli and Geha (1989), supra) which are activated by linear peptide fragments of the allergen. These peptides are created by antigen-presenting cells through antigen processing and are displayed on the cell surface by molecules of the major histocompatibility complex (MHC), where they become available for recognition and binding to the T cell receptor (Schwartz (1985), Annu. Rev. Immunol. 3, 237-255; Rothbart et al. (1989) Int. Immunol. 1, 479-486). In the above step (2), allergen-specific IgE antibodies produced by B cells circulate and bind to FcεRI receptors on mast cells and basophils, thereby serving as the receptor for the allergen. Cross-linking of these cell surface-bound IgE antibodies by allergen represents the signal for the release of preformed and newly synthesized inflammatory mediators and chemotactic substances, leading to the typical allergic inflammatory reaction.

An "individual being sensitised against house-dust mites" is an individual that displays specific IgE antibodies recognising proteins from house-dust mites. An "individual being allergic against house-dust mites" additionally displays allergic symptoms (IgE-mediated) such as immediate symptoms of Type I allergy as mentioned above, when exposed to HDM. As already mentioned above, such allergic reactions or at least sensitisation can also be triggered by exposure to homologous polypeptides which are cross-reactive to the amino acid sequence shown in SEQ ID NO 1. Typically, patients being allergic against HDM show a positive skin prick test (SPT) and a radioallergosorbent test (RAST) of more than 0.35 kUA/L.

A polypeptide is "capable of binding to an antibody" if its affinity to the antibody is significantly higher than that of a reference composition which does not bind to the antibody. The binding of specific IgE antibodies to a particular polypeptide or allergen can be determined by various methods known in the art, e.g. RAST, immunoblot, ELISA, using reference sera from healthy non-allergic individuals (as determined by negative SPT, negative RAST) who do not display allergen-specific IgE antibodies.

The present invention provides novel allergenic structures found in *Dermatophagoides pteronyssinus* and other HDM. The identification of these structures is particularly useful for the selection and production of recombinant allergens that can be employed in the diagnosis and therapy of house-dust mite sensitisation and allergy.

Furthermore, the present invention provides derivatives, analogues and fragments of the polypeptide according to SEQ ID NO 1. Such derivatives may be genetically engineered or chemically synthesised and are generated, e.g. by addition, deletion and/or substitution of one or more amino acids in the sequence shown in SEQ ID NO 1. According to a preferred embodiment, the derivatives, analogues and fragments of the polypeptide according to SEQ ID NO 1 display hypoallergenic properties in comparison to the parent amino acid sequence. Preferably, such polypeptides are generated by the use of a nucleic acid, e.g. a cDNA or mRNA, encoding the respective polypeptide. Such nucleic acids (polynucleotides) have a nucleotide sequence which is derived from the nucleotide sequence shown in SEQ ID NO 2 by addition, deletion and/or deletion of one or more nucleotides.

According to a preferred embodiment of the present invention, the polypeptides are isolated polypeptides, i.e. they are in an essentially pure form. The expression "essentially pure" means that by separation of the polypeptides from other compounds the polypeptides are at least 75% pure, preferably at least 90% pure, more preferably at least 95% pure. The purity of polypeptides can be determined by the skilled person using techniques. known in the art, e.g. by SDS-PAGE followed by protein staining. High Performance Liquid Chromatography (HPLC) and mass spectrometry are methods suitable for analysing polypeptides and short peptides as well.

The polypeptides of the present invention can be prepared in various ways. The polypeptides may be prepared by chemical synthesis, preferably by applying solid phase methods. Methods of chemical peptide synthesis are well known in the art (cf., for example, Merrifield (1963) J. Am. Soc. 85, 2149; Stewart et al. (1984) "Solid Phase Peptide Synthesis", $2^{nd}$ edition, Pearce Chemical Co., Rockford, Ill., USA; Bayer and Rapp (1986) Chem. Pept. Prot. 3, 3; Atherton et al. (1989) "Solid Phase Peptide Synthesis: A Practical Approach", IRL Press, Oxford, UK). These methods are particularly suited for the preparation of short polypeptides having a length of, e.g., 7 to 50 amino acids. Longer polypeptides may be prepared by chemically or enzymatically linking peptide fragments which have been prepared by chemical synthesis. As mentioned above, the polypeptides of the present invention may also be prepared by expression of nucleic acid sequences, in particular DNA sequences in host cells or with the aid of cell-free extracts.

Therefore, the present invention relates also to polynucleotides encoding the above-defined polypeptides. The polynucleotides may be single or double stranded DNA or RNA molecules or nucleic acids derived from DNA and/or RNA species. Thus, according to one embodiment, the polynucleotides of the present invention encode the amino acid sequence shown in SEQ ID NO 1. Due to the degeneracy of the genetic code, many different polynucleotides can be envisaged which encode the amino acid sequence shown in SEQ ID NO 1.

The polynucleotides of the present invention can be used to identify similar sequences in any mite or other species related to Der p and, thus, to identify and isolate sequences which have sufficient homology to hybridise to, e.g., DNA from house-dust or storage mites. This can be carried out, e.g., under conditions of low stringency which leads to hybridisation with sequences having sufficient homology (generally more than 40%), which can be selected for further assessment. Alternatively, high stringency conditions may be applied. In general, high stringency conditions are selected to be about 5° C. to about 10° C. below the thermal melting point $(T_M)$ for the specific sequence at a defined ionic strength and pH. The $T_M$ is the temperature (under defined ionic strength and pH) at which 50% of the target sequence hybridises to a perfectly matched probe. Typical high stringency are those in which the salt concentration is up to about 15 mM Na+(0.1× SSC) at pH 7, and the temperature is at least about 60° C.

In this manner, nucleic acids of the present invention can be used to identify, in other species, in particular other types of HDM or storage mites, sequences encoding peptides or polypeptides having amino acid sequences similar to that of the 14.7 kDa allergen described herein and, thus, to identify allergens in such other species. Therefore, the present invention includes not only the 14.6 kDa protein and other mite allergens encoded by the polynucleotides described herein, but also other mite allergens encoded by polynucleotides which hybridise to the polynucleotide of the present invention.

Accordingly, the present invention relates to polynucleotides comprising a nucleotide sequence having an identity of at least 75%, preferably at least 80%, more preferably at least 90%, most preferred at least 95%, to the nucleotide sequence shown in SEQ ID NO 2. The degree of identity of a polynucleotide sequence to the nucleotide sequence of SEQ ID NO 2 is determined by comparing said polynucleotide sequence and SEQ ID NO 2 using the program "BLAST 2 SEQUENCES (blastn)" (Tatusova et al. (1999) FEMS Microbiol. Lett. 174, 247-250) with the following parameters: reward for a match 1; penalty for a mismatch−2; open gap 5 and extension gap 2 penalties; gap x_dropoff 50; expect 10.0; word size 11; filter; none. According to the present invention the sequence comparison covers at least 50 nucleotides, preferably at least 100 nucleotides, more preferably at least 200 nucleotides; most preferably at least 300 nucleotides.

According to a preferred embodiment of the present invention the polynucleotide comprises the nucleotide sequence shown in SEQ ID NO 2, preferably nucleotides 24 to 434, more preferably nucleotides 81 to 434. In other embodiments, the polynucleotide of the present invention comprises at least 50 contiguous nucleotides, preferably at least 100 nucleotides, more preferably at least 200 nucleotides; most preferably at least 300 nucleotides of the nucleotide sequence shown in SEQ ID NO 2.

The invention also comprises polynucleotides which are degenerate to the polynucleotides described above. The respective complementary strands of the disclosed polynucleotides also form part of the present invention.

The polynucleotides of the present invention are preferably isolated polynucleotides. The polynucleotides are preferably essentially pure, i.e. they are at least 80% pure, more preferably at least 90% pure, most preferably at least 95% pure. The polynucleotides of the present invention can be prepared in various ways (see, e.g., Glick and Pasternack (1994) Molecular Biotechnology, Principles and Applications of Recombination DNA, ASM Press, Washington D.C.; Itakura et al. (1984) Annu. Rev. Biochem. 53, 323-356; Climie et al. (1990) Proc. Natl. Acad. Sci. USA 87, 633-637). The polynucleotides may be synthesised by chemical methods usually employed in oligonucleotide synthesis. PCR based methods can be used to synthesise the polynucleotides of the present invention, in particular longer molecules (see, e.g., Lee et al. (1997) Nucleid Acid Amplification Technologies, Eaton Publishing, Natick, Mass.; USA; McPherson et al. (1996) PCR—A Practical Approach, Vol. 2 and 2, IRL Press, Oxford, UK). Longer polynucleotides can also be prepared by chemically or enzymatically linking fragments which have been synthesised using chemical methods.

A further embodiment of the present invention is a plasmid or vector comprising the above-defined polynucleotide. The plasmids may contain regulatory sequences which facilitate replication of the plasmids or transcription and/or translation of encoded sequences. Examples of such regulatory sequences are promoters, terminator sequences, enhancers etc. The plasmids may also contain nucleotide sequences encoding amino acid sequences facilitating the purification of encoded polypeptides upon expression in a host cell or a cell-free expression system. Examples of such sequences are a 6×His tag, a FLAG tag, and sequences encoding bacterial proteins such as GST. Purification of the encoded polypeptide can be achieved by affinity chromatography using antibodies directed against the respective tags or bacterial sequences. Other affinity matrices (e.g. for purifying polypeptides having a 6×His tag) contain bound metal ions such as $Ni^{2+}$, which are capable to form a chelate complex with the expression tag. Suitable plasmids and vectors containing regulatory and tag sequences or bacterial sequences are known to the skilled person.

The invention further pertains to a cell containing the above defined plasmid or vector and/or a polynucleotide of the present invention. The cells may be selected from plant cells, bacterial cells, yeast cells and other, e.g. mammalian, cells. Preferred are cells allowing for the expression of the genes encoded by the polynucleotides of the present invention. Most preferably, the cells are E. coli cells. The plasmid, vector and/or polynucleotide according to the present invention may be introduced into the cells by techniques known per se, e.g. transformation, transfection etc. The cells can contain the nucleic acid molecules only transiently or stably integrated into their genome. In particular in the latter case, the nucleic acid molecules may be truncated or fragmented due to the process of integration into the genome. Cells containing such truncated or fragmented versions of the nucleic acid molecules fall under the scope of the present invention.

The cells of the present invention can be used for the expression and purification of the polypeptides of the invention. Accordingly, the invention also provides a process for the preparation of a polypeptide described above comprising the step of culturing cells as defined above in a medium under conditions appropriate for the expression of the polypeptide and optionally subsequently recovering the polypeptide from the cells and/or the medium. The cells are preferably cultured in a liquid medium under agitation. If appropriate, expression of the target polypeptide is induced by an inducing agent such as IPTG. Techniques for manipulating cloned DNA molecules and introducing exogenous nucleic acids into a variety of host cells, techniques for transforming these host cells and for expression of foreign nucleotide sequences cloned therein are well known to the person skilled in the art (see, e.g., Sambrook et al. (2001) Molecular Cloning: A Laboratory Manual, $3^{rd}$ edition, Cold Spring Harbour Laboratory Press, Cold Spring Harbour; N.Y., USA; Ausubel et al. (eds.) (1999) Current Protocols in Molecular Biology, $4^{th}$ edition, John Wiley & Sons, New York, USA).

Following cultivation the cells may be disrupted or otherwise opened using established methods and the polypeptide may be recovered by affinity chromatography. Other known methods of protein purification can be employed as well. Exemplary purification steps may include hydroxylapatite, size exclusion, FPLC, and reverse-phase HPLC. Suitable chromatographic media include derivatised dextrans, agarose, cellulose, polyacrylamide, speciality silicas and the like. In a preferred embodiment, the polypeptide of the invention is isolated by a method comprising an affinity chromatography and/or ion exchange chromatography step(s). For affinity chromatography, one or more antibodies directed against the polypeptide of the invention may be immobilised to a solid support. Preferably, the antibody specifically recognises the polypeptide of the invention. Methods for binding antibody molecules to support media are well known in the art. Selection of a particular method is a matter of routine design and is determined in part by the properties of the chosen support material.

Another preferred method of affinity chromatography makes use of adsorption of histidine-rich proteins, e.g. those comprising poly-His tags, on matrices containing bound metal ions. Briefly, a gel is first charged with divalent metal ions to form a chelate. His-rich proteins will be adsorbed to this matrix with differing affinities, depending on the metal ions used, and will be eluted by competitive elution, lowering the pH, or use of strong chelating agents. Within further embodiments of the present invention, a fusion of the polypeptide of interest and an affinity tag may be constructed to facilitate purification. Fusion proteins can be prepared by methods known to a person skilled in the art by preparing each component of the fusion protein and chemically conjugating the components. Alternatively, a polynucleotide encoding the components of the fusion protein in the proper reading frame can be generated using known techniques and expressed by the methods described herein.

Other preferred chromatographic purification steps include ion exchange chromatography, preferably anion exchange chromatography. Example of anion exchange matrices are cellulose, cellulose derivatives or dextran matrices carrying positively chargeable groups such as diethylaminoethyl (DEAE). These and other methods of protein purification are described, e.g. in Deutscher, M. P. (1990) Protein Purification, Academic Press, New York, USA; Scopes (1994) Protein Purification, Springer Verlag, Heidelberg, Germany; Doonan, S. (1996) Protein Purification Protocols, Humana Press.

Polypeptides of the present invention can be used, for example, as "purified allergens". Such purified allergens are useful in the standardisation of allergen extracts which are key reagents for the diagnosis and treatment (or prevention) of house-dust allergy. Furthermore, by using peptides based on fragments of the amino acid sequence shown in SEQ ID NO 1, anti-peptide antisera or monoclonal antibodies can be generated using standard procedures. Such sera or monoclonal antibodies, directed against the 14.7 kDa protein of the present invention, can be used to standardise allergen extracts.

A further embodiment of the present invention is an antibody directed against the above-defined polypeptide. The term "directed against a polypeptide" means that the antibody is capable of binding to the respective polypeptide, i.e. the antibody recognises one or more epitopes determined by the amino acid sequence of the polypeptide. The antibody may be polyclonal or monoclonal. Furthermore, the term "antibody" comprises fragments or derivatives of complete antibodies as long as the affinity for the target polypeptide is preserved. Examples are enzymatically prepared antibody fragments as well as genetically engineered species such as humanised antibodies and single chain antibodies, e.g. scFv constructs. Antibodies of the present invention may be prepared to methods known in the art, e.g. as disclosed in Harlow and Lane (1988) Antibodies: A Laboratory Manual, Cold Spring Harbour Laboratory Press, Cold Spring Harbour, USA. In a preferred embodiment, the antibody is in an essentially pure form, i.e. at least 80% pure, preferably at least 90% pure. In the case of polyclonal antibodies, the antibody composition contains a plurality of different species of antibody molecules.

The antibody is preferably specific for a polypeptide comprising the amino acid sequence shown in SEQ ID NO 1. According to a further preferred embodiment, the antibody of the present invention is directed to one or more epitopes determined by residues 20 to 140 of the amino acid sequence shown in SEQ ID NO 1.

In a particular preferred embodiment of the present invention such epitopes are used for therapy which elicit in the patient to be treated neutralizing antibodies. Such antibodies protect the patient from allergic reactions. Therefore it is possible to identify in a first step regions in the polypeptide which represent probably an epitope e.g. by using hydrophobicity blots. Furthermore, it is tested whether such epitopes have a protective effect in a panel of allergic patients.

Antibodies of the present invention can be used to isolate additional allergenic components of house-dust mites and related species such as storage mites. Such additional allergens can be used for further definition of the characteristics of this family of allergens. Furthermore, anti-peptide sera or monoclonal antibodies directed against the polypeptide of the present invention can be used to standardise and define the content of skin test reagents.

A further embodiment of the present invention is a pharmaceutical composition comprising a polypeptide and/or a polynucleotide and/or an antibody and/or a vector or plasmid and/or a host cell according to the invention, optionally in combination with one or more pharmaceutically acceptable carriers and/or diluents and/or vehicles and/or adjuvants. Of course, the pharmaceutical composition of the invention may contain one or more of each of the above molecules/species.

The materials provided by the present invention, as well as compositions comprising said materials, can be used in methods of diagnosing, treating and preventing HDM allergy. Another aspect of the present invention is therefore the use of a polypeptide and/or a polynucleotide and/or an antibody and/or a vector or plasmid and/or a host cell according to the present invention for the treatment or the prevention or the diagnosis of an allergic disorder. Furthermore, the invention comprises the use of the above embodiments of the present invention for the preparation of a medicament for the treatment or the prevention or the diagnosis of an allergic disorder. Preferably, the materials of the present invention are used for treatment and/or prevention and/or diagnosis (or for the production of a corresponding medicament) of sensitisation or allergy to house-dust mites or storage mites.

The pharmaceutical composition or medicament according to the invention is preferably administered to an individual to be desensitised.

Through the use of the polypeptides of the present invention (as well as polynucleotides encoding the corresponding polypeptides) allergen preparations of consistent, well defined composition and biological activity can be made and administered for therapeutic or preventive purposes (e.g., to modify the allergic response of an individual being sensitised to house-dust mites and/or related species. Such polypeptides or modified versions thereof, in particular hypoallergenic derivatives (e.g. mutants containing one or more amino acid deletions, additions and/or substitutions in comparison to the wild-type sequence as well as chemically modified derivatives), may, for example, modify B cell response and/or T cell response against HDM and related species (e.g. storage mites). As already mentioned above, purified allergens can also be used to design modified derivatives or analogues which are more useful in immunotherapy than are the unmodified naturally occurring (wild-type) peptides or polypeptides.

High doses of allergens generally produce the best symptom relief. However, many patients do not tolerate high doses of allergens because of allergic reactions to the allergens. Therefore, modifications of naturally-occurring allergens can be designed in such a manner that modified polypeptides which have the same or enhanced therapeutic properties as the corresponding wild-type allergen but have reduced side effects, especially hypoallergenic properties such as less or no anaphylactic potential, can be produced. Such modified allergens can be, for example, a polypeptide of the present invention or a modified analogue (e.g. a polypeptide in which the amino acid sequence has been altered to modify immunogenicity and/or reduce allergenicity or to which a component has been added for the same purpose). For example, the polypeptides can be modified using the polyethylene glycol (PEG) method of A. Sehon et al. Short segment deletion or amino acid substitutions of the polypeptide sequence results in a weakened (i.e. reduced or no) antibody binding. Such modifications lead to low IgE binding and are very useful in immunotherapy due to less side effects.

The administration of the (poly)peptides or pharmaceutical compositions (medicaments) of the present invention to an individual, preferably to an individual to be desensitised, can be carried out using known techniques. A peptide or combination of different peptides can be administered to an individual in a composition which includes, e.g., a diluent (such as an appropriate buffer), a carrier and/or an adjuvant. Such composition will generally be administered by injection, oral administration, inhalation, trandermal application or rectal administration. Using the structural information provided by the present invention, it is possible to design a mite polypeptide which, when administered to a HDM sensitive individual in sufficient quantities, will modify the individual's allergic response to a mite allergen. This can be done, for example, by examining the structures of the mite proteins, producing peptides to be examined for their ability to influence B cell and/or T cell responses in HDM sensitive individuals and selecting appropriate epitopes recognised by the cells. Synthetic amino acid sequences which mimic the allergenic epitopes and which are capable of down regulating an allergic response to mite allergens can be used as well.

Polypeptides or antibodies of the present invention can also be used for detecting and diagnosing HDM allergy or sensitisation. For example, by combining blood or blood products obtained from an individual to be assessed for sensitivity to an HDM allergen with an isolated allergenic peptide of mite allergen, under conditions appropriate for binding of components (such as antibodies, T cell, B cells) in the blood with the polypeptide and determining the extent to which such binding occurs.

It is now also possible to design an agent or a drug capable of blocking or inhibiting the ability of mite allergens to induce an allergic reaction in mite-sensitive individuals. Such agents could be designed, for example, in such a manner that they would bind to relevant anti-mite IgEs, thus preventing IgE-allergen binding and subsequent mast cell degranulation. Alternatively, such agents could bind to cellular components of the immune system resulting in suppression or desensitisation of the allergic response to mite allergens. A non-restrictive example of this embodiments of the present invention is the use of appropriate B and T cell epitope peptides, or modifications thereof, based on the cDNA/polypeptide structures of the present invention to suppress the allergic response to HDM allergens. This can be carried out by defining the structures of B and T cell epitope peptides which affect B and T cell function in in vitro studies with blood cells from mite-sensitive individuals.

Finally, the invention relates to kits which are useful for the diagnosis, treatment and/or prevention of an allergic disorder comprising a polypeptide and/or a polynucleotide and/or an antibody and/or a vector or plasmid and/or a host cell according to the present invention. The materials provided by the present invention, as well as compositions and kits containing these materials, can be used in methods of diagnosing, treating and preventing allergy or sensitisation against HDM or related species such as storage mites.

The present invention is based on a recombinant DNA molecule and fragments thereof coding for a 14.7 kDa allergen from the house-dust mite *Dermatophagoides pteronyssinus* (Der p). The novel mite allergen can be used for diagnosis of HDM allergic patients as well as for therapy. According to the present invention it could be shown that the new mite allergen induces a strong and specific IgG response in rabbits, indicating that specific immunotherapy with this new mite allergen will induce blocking IgG antibodies in humans. The use of hypoallergenic derivatives generated on the basis of the sequence of this new allergen for immunotherapy could additionally reduce the risk of anaphylactic side effects (3).

The figures show:

FIG. 1A shows the cDNA (SEQ ID NO 2) and deduced amino acid sequence (SEQ ID NO 1) of the preferred allergen according to the invention. The start codon, the stop codon and the polyadenylation signal are underlined. The sequence coding for the signal sequence (amino acids 1 to 19) comprises nucleotides 24 to 80. The cleavage site is between amino acid residues 19 (G) and 20 (F) (bold). The numbers on the left side of the sequence indicate the nucleotide positions and those on the right side of the sequence the amino acid positions.

FIG. 1B shows a Coomassie Blue stained SDS-PA gel and the result of mass spectrometric analysis of the identified allergen. Left: Coomassie Blue stained SDS-PAGE gel. In lane 1, a molecular mass marker and in lane 2, 3 µg of purified allergen are displayed. Right: MS analysis of the purified allergen according to the invention. The mass/charge ratio is shown on the x-axis and the signal intensity is displayed on the y-axis as the percentage of the most intense signal obtained in the investigated mass range. The peak at 14724.9 corresponds to the calculated mass of the deduced amino acid sequence of 14726.1.

FIG. 2A shows the IgE reactivity of the new mite allergen. The identified allergen was dotted onto nitrocellulose strips and incubated with sera from Der p allergic patients. Bound IgE were detected with $^{125}$I-labelled anti-human IgE antibodies.

Figure 2B:
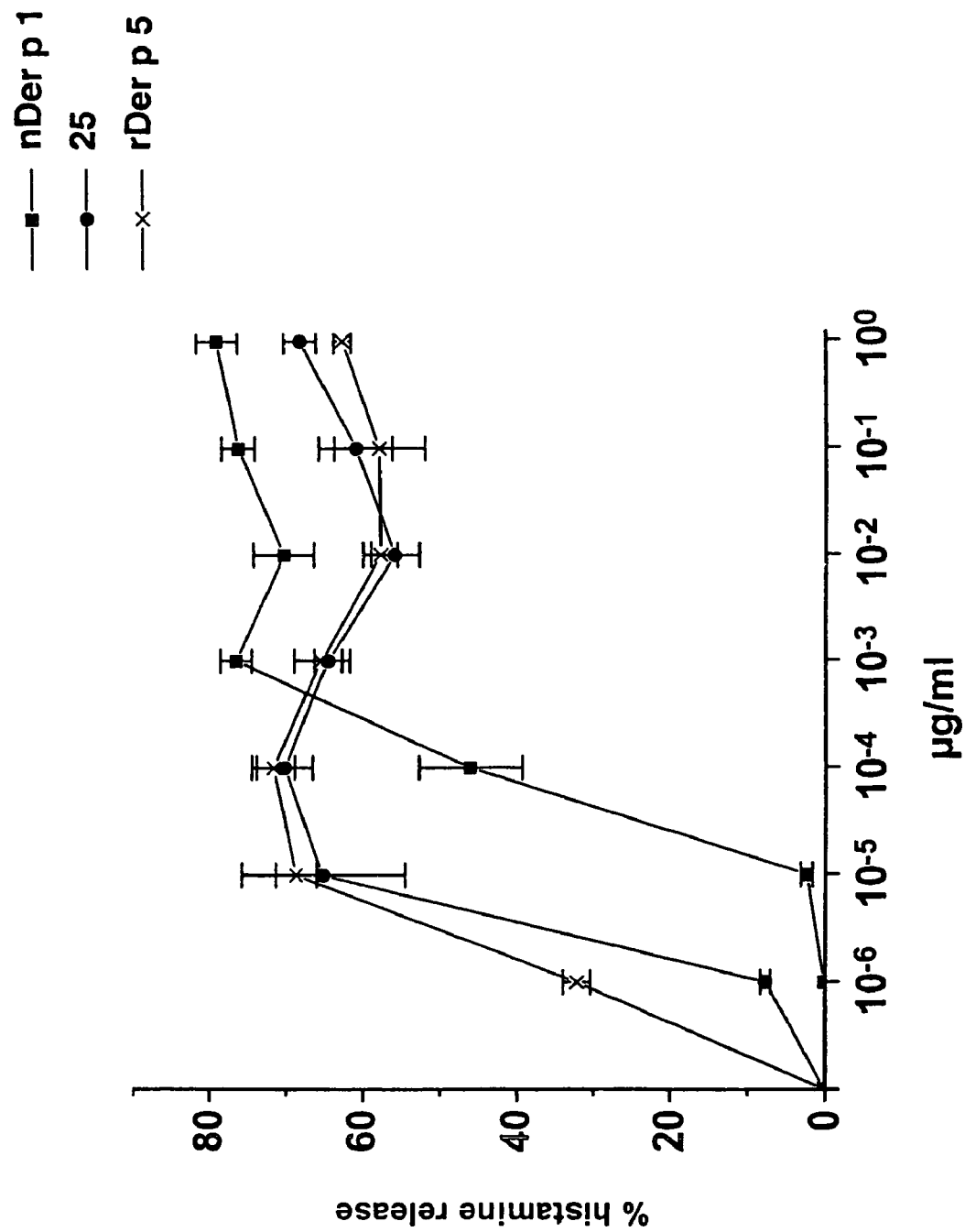

FIG. 2B demonstrates the induction of histamine release from basophils of a Der p allergic patient. Granulocytes of a Der p allergic patient were incubated with various concentrations of nDer p 1, allergen according to the invention and rDer p 5 (x-axis). The percentage of histamine released into the cell-free culture supernatant is shown on the y-axis.

FIG. 3A shows an alignment of the amino acid sequence of the allergen according to the present invention (SEQ ID NO 1) with homologous dust mite allergens. The amino acid sequence of the allergen according to the invention was compared with the group 5 allergens from *Lepidoglyphus destructor* (Lep d 5) (SEQ ID NO 3), *Blomia tropicalis* (Blo t 5) (SEQ ID NO 4) and *Dermatophagoides pteronyssinus* (Der p 5)

(SEQ ID NO 5). Amino acids identical to the allergen of the invention are indicated with hyphens and points represent gaps introduced for maximal fit.

Figure 3B:
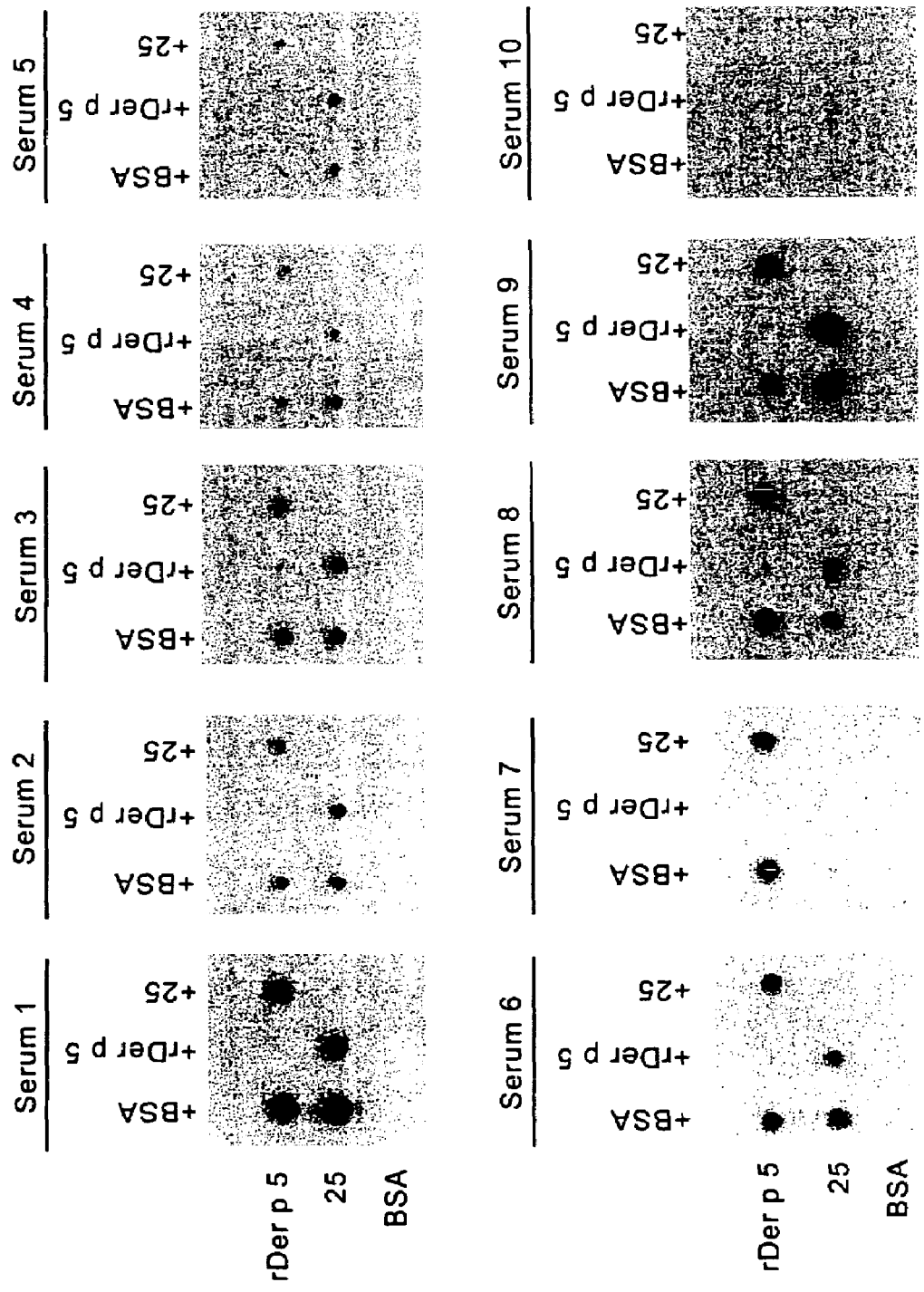

FIG. 3B demonstrates the lack of cross-reactivity between the novel mite allergen and Der p 5. Sera from Der p allergic patients (1-9) and one non-allergic patient (10) were preadsorbed with BSA, rDer p 5 and the allergen according to the invention, respectively. Recombinant Der p 5, the novel mite allergen and BSA were dotted on nitrocellulose strips, incubated with the preadsorbed sera and bound IgE were detected with $^{125}$I-labelled anti-human IgE antibodies.

Figure 4:
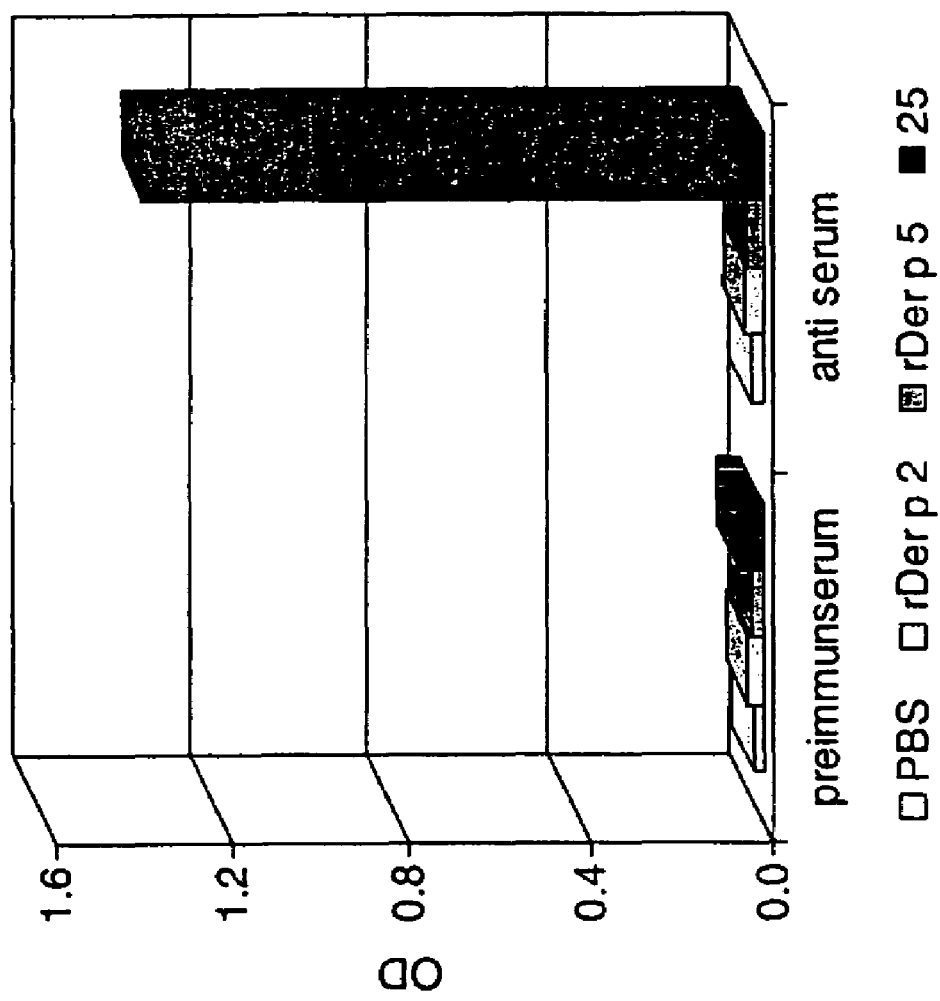

FIG. 4 shows the IgG-reactivity of a rabbit anti serum raised against the newly identified allergen with different Der p allergens. Preimmunserum and anti serum were tested for IgG reactivity to PBS (as control), rDer p 2, rDer p 5 and the allergen of the invention.

The present invention is further illustrated by the following non-limiting examples.

EXAMPLES

Example 1

Expression and Purification of a New Recombinant *Dermatophagoides pteronyssinus* Allergen The cDNA of clone 25 (FIG. 1A) coding for the mature new allergen was cloned into the expression vector pET-1 7b (Novagene, Madison, Wis.) and expressed in *Escherichia coli* BL21 (DE3) (Stratagene, La Jolla, Calif.). The bacterial cells were grown to an $OD_{600}$ of 0.6 to 0.8 in LB-medium containing 100 mg/ml ampicillin. The expression of the recombinant protein was induced by adding isopropyl-β-thiogalactopyranoside (IPTG) to a final concentration of 0.5 mM and cultured for additional 3 hours at 37° C. The *E. coli* cells from 1 liter culture were harvested by centrifugation, resuspended in 10 ml 25 mM Imidazole pH7.4, 0.1% Triton X 100 and treated with 100 µg lysozyme for 20 min at room temperature. The lysate of the bacterial cells was frozen in liquid nitrogen and defrosted in a 50° C. water bath. The genomic DNA was degraded by addition of 1 µg DNase for 10 min at room temperature and reaction was stopped with 200 µl 5M NaCl. A fraction containing the soluble proteins was obtained after centrifugation of the lysed bacterial cells at 18,000 rpm (Sorval RC5C, SS34) for 20 min at 4° C. The soluble fraction, containing the clone 25-derived allergen was dialyzed against buffer A (10 mM Tris-CI pH 7.0, 4% isopropanol, 1 ml/l phenyl-methyl-sulfonyl-fluoride, PMSF) and applied to a DEAE Sepharose Fast Flow column (Amersham Biosciences, Uppsala, Sweden). The clone 25-derived allergen was eluted by a 0-500 mM NaCl gradient. Fractions containing the recombinant allergen were pooled, dialyzed against buffer B (10 mM $Na_2HPO_4$ pH 4.0, 5 mM β-mercaptoethanol, 1 ml/l PMSF) and applied to a SP Sepharose Fast Flow column (Amersham Biosciences). The clone 25 derived allergen was eluted by a combined pH 4.0-7.0 and 0-500 mM NaCl gradient and fractions containing more than 90% pure clone 25 encoded allergen were pooled, dialyzed against 10 mM $Na_2HPO_4$ pH 7.0 and stored at −20° C. Protein samples were analysed for purity by sodium dodecyl sulfate-polyacrylamide gel electrophoresis (SDS-PAGE) and Coomassie Blue protein staining (FIG. 1B).

Example 2

IgE Binding Capacity and Biological Activity of the New Der p Allergen (i) The New Allergen Binds IgE from Mite Allergic Patients Sera The IgE binding capacity of the new Der p allergen encoded by the clone 25 cDNA was analysed by dot blot experiments using sera from 117 mite allergic patients. The new allergen was dotted onto nitrocellulose strips (1 µg/dot) and the strips were incubated with sera of Der p allergic patients. Bound IgE antibodies were detected with $^{125}$I-labelled anti-human IgE antibodies.

Thirty out of the 117 sera (26%) showed IgE binding to the new Der p allergen (FIG. 2A).

(ii) The New Der p Allergen Induces Histamine Release from Mite Allergic Patients' Basophils The major allergen nDer p 1 (4) and the minor allergen rDer p 5 (5) from the house dust mite Der p were compared with the new allergen encoded by the clone 25 cDNA for their capacity to induce histamine release from basophils of a Der p allergic individual.

Granulocytes were isolated from heparinized blood samples of a Der p allergic individual by dextran sedimentation. Cells were incubated with increasing concentrations ($10^{-6}$ to 1 µg/ml) of nDer p 1, rDer p 5 and clone 25-derived allergen, respectively. Histamine released in the cell-free culture supernatant was measured by radioimmunoassay (Immunotech, Marseille, France) and indicated as percentage of total histamine release. Results are displayed as mean values of triplicate determinations. As shown in FIG. 2, the new allergen encoded by the clone 25 cDNA as well as rDer p 5 induced maximal histamine release already at 10 pg/ml, whereas the major allergen nDer p 1 induced maximal histamine release only at a concentration of 1 ng/ml.

Example 3

The New Recombinant Allergen Lacks Cross-Reactivity to Der p 5

The new allergen encoded by clone 25 shows homology to other dust mite allergens (FIG. 3A), namely to the group 5 allergens from *Lepidoglyphus destructor* (Lep d 5), *Blomia tropicalis* (Blo t 5) and *Dermatophagoides pteronyssinus* (Der p 5). Because of the amino acid identity of 30% between the new allergen and Der p 5, the clone 25-derived allergen belongs to a so far unknown new group of dust mite allergens. Dot blot inhibition experiments demonstrated that Der p 5 and the new allergen do not share IgE epitopes. One pg of Der p 5, the clone 25-derived allergen and BSA were dotted onto nitrocellulose strips. The strips were incubated with nine patients sera with reactivity both to Der p 5 and the new allergen and with one serum of a non-allergic patient which were preadsorbed with 10 pg/ml each of rDer p 5, the clone 25-derived allergen and BSA. Bound IgE antibodies were detected with $^{125}$I-labelled anti-human IgE antibodies (FIG. 3B).

Preadsorption of sera from mite allergic patients with the new allergen inhibits IgE binding to the dotted new allergen and also preadsorption of the sera with rDer p 5 inhibits IgE binding to the dotted rDer p 5. However, preadsorption of rDer p 5 did not inhibit IgE binding to the new allergen and vice versa, demonstrating a lack of cross-reactivity between rDer p 5 and the new allergen.

Example 4

Immunization with the New Mite Allergen Induces IgG Antibodies in Rabbits that Recognize the New Allergen In order to test whether the new mite allergen is immunogenic, one rabbit was immunized with the new allergen using Freund's adjuvant. The rabbit was immunized with 200 μg/injection using once Freund's complete and twice incomplete adjuvants (Charles River, KiBlegg, Germany).

The induction of IgG antibodies was studied by ELISA. Recombinant Der p 2, rDer p 5 and the clone 25-derived allergen, each at a concentration of 5 pg/ml, were coated on an ELISA plate (Nunc, Roskilde, Denmark) overnight at 4° C. and then incubated with the 1:10000 diluted rabbit clone 25-derived allergen anti serum and a rabbit preimmunserum as control. Bound rabbit antibodies were detected with HRP-conjugated donkey anti rabbit Ig antibodies (Amersham).

High titers of specific IgG antibodies were induced with the new mite allergen. The antiserum induced with the clone 25-derived allergen reacts specifically with the clone 25-derived allergen and no cross-reactivity with rDer p 2 and rDer p 5 could be detected (FIG. 4).

REFERENCES

1. Fernandez-Caldas E. Mite species of allergologic importance in Europe. Allergy 1997; 52:383-6.
2. Thomas W R, Smith W A, Hales B J, Mills K L, O'Brien R M. Characterization and immunobiology of house dust mite allergens. Int Arch Allergy Immunol 2002; 129:1-18.
3. Valenta R. The future of antigen-specific immunotherapy of allergy. Nat Rev Immunol 2002; 2:446-53.
4. Hales B J, Shen H, Thomas W R. Cytokine responses to Der p 1 and Der p 7: house dust mite allergens with different IgE-binding activities. Clin Exp Allergy 2000; 30:934-43.
5. Lin K L, Hsieh K H, Thomas W R, Chiang B L, Chua K Y. Characterization of Der p V allergen, cDNA analysis, and IgE-mediated reactivity to the recombinant protein. J Allergy Clin Immunol 1994; 94:989-96.

---

The invention claimed is:

1. An isolated polypeptide comprising the amino acid sequence shown in SEQ ID NO: 1.

2. An isolated polypeptide comprising the amino acids 20 to 140 shown in SEQ ID NO: 1.

3. An isolated polypeptide consisting of between 8 and 140 consecutive amino acid residues of SEQ ID NO:1 and, which in a rabbit model, induces IgG antibodies that do not cross-react with *Dermatophagoides pteronyssinus* (Der p) 2 or Der p 5.

4. The isolated polypeptide according to claim 3, which consists of between 18 and 140 consecutive amino acids of the amino acid sequence shown in SEQ ID NO: 1.

5. The isolated polypeptide of claim 3, which consists of between 21 and 140 consecutive amino acids of SEQ ID NO:1.

6. The isolated polypeptide of claim 3, which consists of between 25 and 140 consecutive amino acids of SEQ ID NO:1.

7. The isolated polypeptide of claim 3, which consists of between 35 and 140 consecutive amino acids of SEQ ID NO:1.

8. The isolated polypeptide of claim 3, which consists of between 50 and 140 consecutive amino acids of SEQ ID NO:1.

9. The isolated polypeptide of claim 3, which consists of between 8 and 100 consecutive amino acids of SEQ ID NO:1.

10. A protein fusion comprising the polypeptide of one of claims 1, 2, or 3.

11. A pharmaceutical composition comprising the polypeptide according to one of claims 1, 2, or 3 and one or more pharmaceutically acceptable carriers, diluents, vehicles or adjuvants.

12. A diagnostic kit comprising a container and the polypeptide according to one of claims 1, 2, or 3.

* * * * *

SEQUENCE LISTING

<160> NUMBER OF SEQ ID NOS: 5

<210> SEQ ID NO 1
<211> LENGTH: 140
<212> TYPE: PRT
<213> ORGANISM: Dermatophagoides pteronyssinus

<400> SEQUENCE: 1

```
Met Lys Phe Ile Ile Thr Leu Phe Ala Ala Ile Val Met Ala Ala Ala
1               5                   10                  15

Val Ser Gly Phe Ile Val Gly Asp Lys Lys Glu Asp Glu Trp Arg Met
            20                  25                  30

Ala Phe Asp Arg Leu Met Met Glu Glu Leu Glu Thr Lys Ile Asp Gln
        35                  40                  45

Val Glu Lys Gly Leu Leu His Leu Ser Glu Gln Tyr Lys Glu Leu Glu
    50                  55                  60

Lys Thr Lys Ser Lys Glu Leu Lys Glu Gln Ile Leu Arg Glu Leu Thr
65                  70                  75                  80

Ile Gly Glu Asn Phe Met Lys Gly Ala Leu Lys Phe Phe Glu Met Glu
                85                  90                  95

Ala Lys Arg Thr Asp Leu Asn Met Phe Glu Arg Tyr Asn Tyr Glu Phe
            100                 105                 110

Ala Leu Glu Ser Ile Lys Leu Leu Ile Lys Lys Leu Asp Glu Leu Ala
        115                 120                 125

Lys Lys Val Lys Ala Val Asn Pro Asp Glu Tyr Tyr
    130                 135                 140
```

<210> SEQ ID NO 2
<211> LENGTH: 473
<212> TYPE: DNA
<213> ORGANISM: Dermatophagoides pteronyssinus

<400> SEQUENCE: 2

```
aaaaaaagaa attttttca aaatgaaat  tcatcattac cctttcgct  gccattgtaa      60 tggctgctgc cgtatctggt tttattgttg gtgacaaaaa agaagatgaa tggcgtatgg     120
cattcgatcg tttaatgatg gaagaattgg aaacaaaaat cgatcaagtt gaaaaaggtt     180
```

-continued

```
tacttcatct tagtgaacaa gaacaaattc ttcgtgaact tactattggt gaaaatttta    240
tgaaaggtgc attaaaattt ttcgaatgg  aagctaaacg taccgattta aatatgtttg    300
aacgatacaa ttatgaattt gctttggaaa gtattaaatt attgattaaa aaattggacg    360
aattggctaa aaaagttaaa gctgtaaatc cggatgaata ttattaattt aatcgacatt    420
taatccaaaa atgtttccaa aataaaaatt ttctcttata aaaaaaaaaa aaa           473
```

<210> SEQ ID NO 3
<211> LENGTH: 110
<212> TYPE: PRT
<213> ORGANISM: Lepidoglyphus destructor

<400> SEQUENCE: 3

```
Asp Asp Phe Arg Asn Glu Phe Asp Arg Leu Leu Ile His Met Thr Glu
1               5                   10                  15

Glu Gln Phe Ala Lys Leu Glu Gln Ala Leu Ala His Leu Ser His Gln
            20                  25                  30

Val Thr Glu Leu Glu Lys Ser Lys Ser Lys Glu Leu Lys Ala Gln Ile
        35                  40                  45

Leu Arg Glu Ile Ser Ile Gly Leu Asp Phe Ile Asp Ser Ala Lys Gly
    50                  55                  60

His Phe Glu Arg Glu Leu Lys Arg Ala Asp Leu Asn Leu Ala Glu Lys
65                  70                  75                  80

Phe Asn Phe Glu Ser Ala Leu Ser Thr Gly Ala Val Leu His Lys Asp
                85                  90                  95

Leu Thr Ala Leu Ala Thr Lys Val Lys Ala Ile Glu Thr Lys
            100                 105                 110
```

<210> SEQ ID NO 4
<211> LENGTH: 134
<212> TYPE: PRT
<213> ORGANISM: Blomia tropicalis

<400> SEQUENCE: 4

```
Met Lys Phe Ala Ile Val Leu Ile Ala Cys Phe Ala Ala Ser Val Leu
1               5                   10                  15

Ala Gln Glu His Lys Pro Lys Lys Asp Asp Phe Arg Asn Glu Phe Asp
            20                  25                  30

His Leu Leu Ile Glu Gln Ala Asn His Ala Ile Glu Lys Gly Glu His
        35                  40                  45

Gln Leu Leu Tyr Leu Gln His Gln Leu Asp Glu Leu Asn Glu Asn Lys
    50                  55                  60

Ser Lys Glu Leu Gln Glu Lys Ile Ile Arg Glu Leu Asp Val Val Cys
65                  70                  75                  80

Ala Met Ile Glu Gly Ala Gln Gly Ala Leu Glu Arg Glu Leu Lys Arg
                85                  90                  95

Thr Asp Leu Asn Ile Leu Glu Arg Phe Asn Tyr Glu Glu Ala Gln Thr
            100                 105                 110

Leu Ser Lys Ile Leu Leu Lys Asp Leu Lys Glu Thr Glu Gln Lys Val
        115                 120                 125

Lys Asp Ile Gln Thr Gln
    130
```

<210> SEQ ID NO 5
<211> LENGTH: 132
<212> TYPE: PRT

```
<213> ORGANISM: Dermatophagoides pteronyssinus

<400> SEQUENCE: 5

Met Lys Phe Ile Ile Ala Phe Phe Val Ala Thr Leu Ala Val Met Thr
1               5                   10                  15

Val Ser Gly Glu Asp Lys Lys His Asp Tyr Gln Asn Glu Phe Asp Phe
                20                  25                  30

Leu Leu Met Glu Arg Ile His Glu Gln Ile Lys Lys Gly Glu Leu Ala
            35                  40                  45

Leu Phe Tyr Leu Gln Glu Gln Ile Asn His Phe Glu Glu Lys Pro Thr
        50                  55                  60

Lys Glu Met Lys Asp Lys Ile Val Ala Glu Met Asp Thr Ile Ile Ala
65                  70                  75                  80

Met Ile Asp Gly Val Arg Gly Val Leu Asp Arg Leu Met Gln Arg Lys
                85                  90                  95

Asp Leu Asp Ile Phe Glu Gln Tyr Asn Leu Glu Met Ala Lys Lys Ser
                100                 105                 110

Gly Asp Ile Leu Glu Arg Asp Leu Lys Lys Glu Glu Ala Arg Val Lys
            115                 120                 125

Lys Ile Glu Val
        130
```